United States Patent
Loy et al.

(10) Patent No.: US 11,325,925 B2
(45) Date of Patent: May 10, 2022

(54) DIHYDROPYRIDAZINE ANTIOXIDANT SUNSCREENS

(71) Applicant: ARIZONA BOARD OF REGENTS ON BEHALF OF THE UNIVERSITY OF ARIZONA, Tucson, AZ (US)

(72) Inventors: Douglas A. Loy, Tucson, AZ (US);
Robb E. Bagge, Tucson, AZ (US);
Wenmo Sun, Tucson, AZ (US);
Nanayakkarawasan Pallage Ravindu Nanayakkara, Tucson, AZ (US)

(73) Assignee: ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 157 days.

(21) Appl. No.: 16/643,809

(22) PCT Filed: Sep. 4, 2018

(86) PCT No.: PCT/US2018/049357
§ 371 (c)(1),
(2) Date: Mar. 2, 2020

(87) PCT Pub. No.: WO2019/046848
PCT Pub. Date: Mar. 7, 2019

(65) Prior Publication Data
US 2020/0270281 A1    Aug. 27, 2020

Related U.S. Application Data

(60) Provisional application No. 62/553,437, filed on Sep. 1, 2017.

(51) Int. Cl.
*C07F 7/08*     (2006.01)
*A61Q 17/04*    (2006.01)
(Continued)

(52) U.S. Cl.
CPC ............ *C07F 7/0812* (2013.01); *A61K 8/585* (2013.01); *A61Q 17/04* (2013.01); *C08F 279/02* (2013.01); *C09D 5/32* (2013.01); *A61K 2800/522* (2013.01)

(58) Field of Classification Search
CPC .................. C07F 7/0812; A61K 8/585; A61K 2800/522; A61Q 17/04; C08F 279/02;
(Continued)

(56) References Cited

U.S. PATENT DOCUMENTS 8,552,183 B2    10/2013  Wiessler et al.
10,731,018 B2 *  8/2020  Loy ........................ C08F 36/045
(Continued)

FOREIGN PATENT DOCUMENTS

WO    WO2017027521 A2    2/2017

OTHER PUBLICATIONS

Bagge et al. "Transforming Polybutadiene with Tetrazine Click Chemistry into Antioxidant Foams That Fluoresce with Oxidation" Chemistry of Materials. Aug. 30, 2017 (Aug. 30, 2017) vol. 29, p. 7953-7960; p. 7953, abstract, p. 7954, left col. para 2.

*Primary Examiner* — Joseph D Anthony
(74) *Attorney, Agent, or Firm* — Nguyen Tarbet LLC

(57) ABSTRACT

Herein polymers and particles which comprise a plurality of dihydropyridazine or hydropyridazine functional groups are described. Methods for their formation and specific monomers which may be used in their formation are also described. The polymers and particles are UV absorbing, hydrogen-donor antioxidant materials which signal a depletion of antioxidant ability by a decrease in visible fluorescence. These polymers and particles may be used as UV protectants for a variety of materials and substrates and may even be used in a topically applied formulation for human skin.

12 Claims, 2 Drawing Sheets

---

Provide a UV absorbing dihydropyridazine or hydropyridazine monomer.

Provide an orthosilicate co-monomer

React monomer and co-monomer to form an organosilicon particle

(51) Int. Cl.
*A61K 8/58* (2006.01)
*C09D 5/32* (2006.01)
*C08F 279/02* (2006.01)

(58) Field of Classification Search
CPC .... C08F 136/06; C08F 136/08; C08F 136/18; C09D 5/32; C09D 151/003; C08C 19/22; C08G 77/54; C07D 237/04
See application file for complete search history.

(56) References Cited

U.S. PATENT DOCUMENTS

| | | | |
|---|---|---|---|
| 10,851,192 B2* | 12/2020 | Loy | C08F 236/20 |
| 2018/0244820 A1* | 8/2018 | Loy | C07D 237/04 |
| 2018/0291170 A1* | 10/2018 | Loy | C08J 9/02 |

* cited by examiner

```
┌─────────────────────────────────────────────────────────────────────┐
│ Provide a UV absorbing dihydropyridazine or hydropyridazine monomer.│
└─────────────────────────────────────────────────────────────────────┘
                                  ▽
┌─────────────────────────────────────────────────────────────────────┐
│                   Provide an orthosilicate co-monomer               │
└─────────────────────────────────────────────────────────────────────┘
                                  ▽
┌─────────────────────────────────────────────────────────────────────┐
│      React monomer and co-monomer to form an organosilicon particle │
└─────────────────────────────────────────────────────────────────────┘
```

FIG. 1

```
┌─────────────────────────────────────────────────────────────────────┐
│          Provide a polymer comprising alkenyl or alkynyl groups     │
└─────────────────────────────────────────────────────────────────────┘
                                  ▽
┌─────────────────────────────────────────────────────────────────────┐
│                   Provide a 1,2,4,5-tetrazine monomer               │
└─────────────────────────────────────────────────────────────────────┘
                                  ▽
┌─────────────────────────────────────────────────────────────────────┐
│ React said polymer and monomer in a Carboni-Lindsey reaction to form│
│                        a functionalized polymer                     │
└─────────────────────────────────────────────────────────────────────┘
```

FIG. 2

DIHYDROPYRIDAZINE ANTIOXIDANT SUNSCREENS

CROSS REFERENCE

This application claims priority to U.S. Provisional Patent Application No. 62/553,437, filed Sep. 1, 2017, the specifications of which are incorporated herein in their entirety by reference.

FIELD OF THE INVENTION

The present invention relates to polymers and particles which comprise a plurality of dihydropyridazine or hydropyridazine functional groups and are UV absorbing, hydrogen-donor antioxidant materials which signal a depletion of antioxidant ability by a decrease in visible fluorescence.

BACKGROUND OF THE INVENTION

UV absorbing polymers and particles have been widely used for UV protection of various materials, substrates and even human skin. Various desirable characteristics of an ideal UV protectant have been identified. These characteristics include: broad absorbance in both UVA (320-400 nm) and UVB (290-320 nm) regions, resistance to UV degradation, and antioxidant properties.

While advances have been made in the design of long-lasting, UV-stable formulations, it is difficult to effectively gauge the degree of degradation of a UV protectant. Lack of certainty of the lifetime of an applied formulation can lead to either wasteful and expensive over-frequent application or to unnecessary damage of the protected material between expiration of one treatment and application of the next.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention addresses this difficulty in monitoring UV protectant degradation by use of sunscreen polymers and particles which exhibit a degradation-dependent decrease in visible fluorescent intensity. The sunscreen protectant is fluorescent before oxidation but significantly less fluorescent after oxidation. Upon reaction as an antioxidant or degradation by UV irradiation, the fluorescent functional group is changed and the fluorescent intensity of the protectant layer is decreased.

One of the unique and inventive technical features of the present invention is the use of dihydropyridazine or hydropyridazine functional groups in UV protectant polymers or particles. Without wishing to limit the invention to any theory or mechanism, it is believed that the technical feature of the present invention advantageously provides for the ability to simultaneously absorb UVA and UVB light, act as an antioxidant, and report a degree of degradation by fluorescence. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which:

FIG. 1 shows a non-limiting example flowchart for a method of forming a UVA and UVB absorbing organosilicon particle.

FIG. 2 shows a non-limiting example flowchart for a method of forming an UVA and UVB absorbing modified polymer.

DESCRIPTION OF PREFERRED EMBODIMENTS

Figure 3:
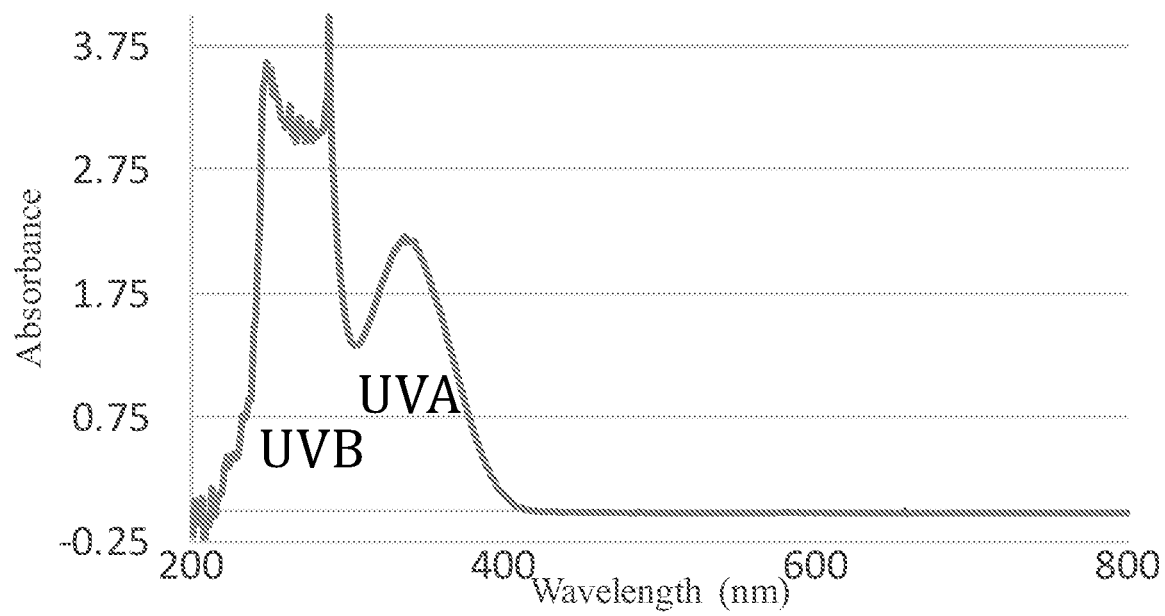
FIG. 3 shows a non-limiting example UV absorbance spectrum of a 1M solution of dimethyl 1,2,4,5-dihydropyridazine-3,6-dicarboxylate. The spectrum shows strong absorbance in the UVA and UVB regions and no absorbance in the visible region.

The present invention relates to polymers and particles which comprise a plurality of dihydropyridazine or hydropyridazine functional groups and are UV absorbing, hydrogen-donor antioxidant materials which signal a depletion of antioxidant ability by a decrease in visible fluorescence. In some embodiments, these polymers and particles may absorb UVA and UVB better than most commercial sunscreens. In further embodiments, the UV absorbing materials may be applied as a thin film or as a plurality of particles dispersed in water, alcohol, oil, solvents or an adhesive.

According to one embodiment, the present invention features an antioxidant, UVA and UVB absorbing monomer, wherein the monomer may comprise a dihydropyridazine or hydropyridazine functional group, the monomer may further comprise at least one alkoxysilane functional group and the monomer may be configured to react with one or more co-monomers to form a UV absorbing organosilicon particle.

According to another embodiment, the present invention features a UV absorbing organosilicon particle, wherein the particle may comprise a plurality of dihydropyridazine or hydropyridazine functional groups, and the particle may be configured to absorb UVA and UVB light.

In still another embodiment, the present invention may feature a method of forming a UV absorbing organosilicon particle, wherein the particle comprises a plurality of dihydropyridazine or hydropyridazine functional groups, and wherein the particle is configured to absorb UVA and UVB light, the method comprising: providing a UV absorbing monomer, wherein the monomer comprises a dihydropyridazine or hydropyridazine functional group, and wherein the monomer comprises at least one alkoxysilane functional group; providing an orthosilicate co-monomer; and mixing said monomer and co-monomer, wherein the monomer and co-monomer react in a condensation reaction to form said organosilicon particle.

In a further embodiment, the present invention may feature a UV absorbing modified polymer, wherein the polymer comprises a plurality of dihydropyridazine or hydropyridazine functional groups, wherein said modified polymer comprises at least one segment according to the following structure:

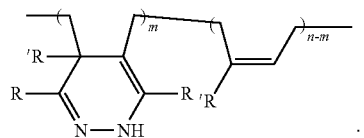

R = H, CO$_2$Alkyl, Alkyl, Aryl
R' = H, Cl, CH$_3$
n = 1-100,000
m = 0.00001n-1.0n In yet further embodiments, the present invention may feature a method of forming a UV absorbing modified polymer, wherein the polymer comprises a plurality of dihydropyridazine or hydropyridazine functional groups, the method comprising: providing a polymer comprising a plurality of alkenyl or alkynyl functional groups; providing a 1,2,4,5-tetrazine monomer, wherein the monomer is a dialkyl 1,2,4,5-tetrazine-3,6-dicarboxylate; and mixing said polymer with said monomer, wherein the 1,2,4,5-tetrazine reacts with the alkenyl or alkynyl functional groups in a Carboni-Lindsey reaction to form said modified polymer.

In preferred embodiments, the dihydropyridazine or hydropyridazine functional groups may be capable of being oxidized to one or more pyridazine functional groups by consuming one or more surrounding oxidizing species, thereby providing the monomer an ability to act as an antioxidant, the dihydropyridazine or hydropyridazine functional groups may be fluorescent and the pyridazine functional groups less fluorescent, an oxidation of said dihydropyridazine or hydropyridazine functional groups may cause a depletion of said ability to act as an antioxidant, and said oxidation may be detected by a decrease of a fluorescent intensity of the monomer, particle or polymer.

According to one embodiment, the co-monomer may comprise an alkyl orthosilicate. Non-limiting examples of alkyl orthosilicates include tetraethyl orthosilicate and tetramethyl orthosilicate. In further embodiments, the UV absorbing monomer may comprise a dialkyl 1,2,4,5-dihydropyridazine-3,6-dicarboxylate derivative. According to still further embodiments, a catalyst may be used in a reaction between the monomer and co-monomer. In selected embodiments the monomer may comprise at least one of the following structures:

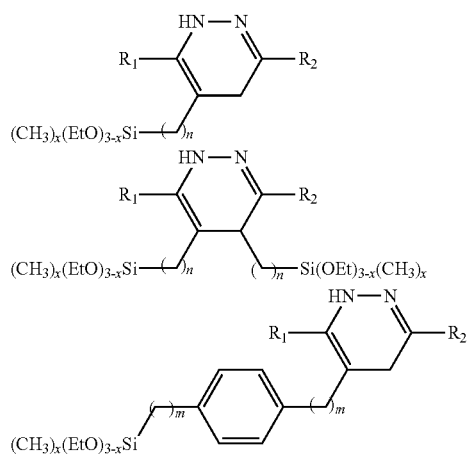

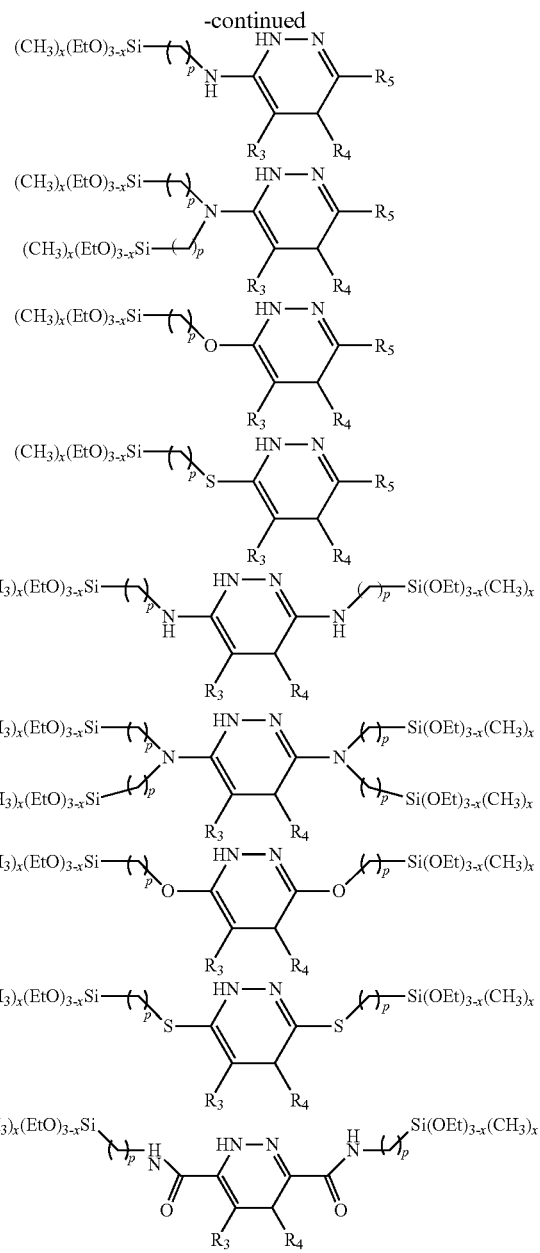

n = 0-2  m = 0-3
X = 0-2  R$_1$ = R$_2$ or R$_1$ ≠ R$_2$  p = 1-4
R$_1$ = H, alkyl, aryl, CO$_2$alkyl, NHAlkyl, Ndialkyl, Cl, Oalkyl, Oaryl, Salkyl
R$_2$ = H, alkyl, aryl, CO$_2$alkyl, NHAlkyl, Ndialkyl, Cl, Oalkyl, Oaryl, Salkyl
R$_3$ = R$_4$ or R$_3$ ≠ R$_4$
R$_3$ = H, alkyl, aryl
R$_4$ = H, alkyl, aryl
R$_5$ = H, alkyl, aryl, Oalkyl, Salkyl, 1°, 2° alkyl or aryl amine, CN, Cl, CO$_2$alkyl In some embodiments, the monomer, particle or polymer may comprise a UV protectant, sunscreen, polymer additive or paint additive or may be configured to protect a substrate from UV exposure. As a non-limiting example the monomer, particle or polymer may comprise a protective coating for a polymer, eyeglass lens, metal or skin. In preferred embodiments, the monomer, particle or polymer may be configured to absorb UVA and UVB light.

According to some embodiments, oxidation may cause the monomer, particle or polymer to have a decreased ability to absorb UV light. In other preferred embodiments, the monomer, particle or polymer may be colorless before and after oxidation. Without wishing to limit the invention to a particular theory or mechanism, this may allow for inconspicuous coating of a variety of surfaces.

In additional embodiments, the polymer comprising a plurality of alkenyl or alkynyl groups may be polybutadiene, polyisoprene or polychloroprene. In other embodiments, the polymer may be a block copolymer comprising at least one segment which does not comprise dihydropyridazine or hydropyridazine functional groups. In still other embodiments, the alkenyl or alkynyl functional groups may be either pendant from or part of a polymer backbone. According to some embodiments, the polymer may comprise a particle, film, foam, or powder. In one embodiment, about 1-100% of the alkenyl or alkynyl functional groups react with the tetrazine monomers. In other embodiments, about 1-5%, 5-10%, 10-20%, 20-30%, 30-40%, 40-50%, 60-70%, 70-80%, 80-90% or 90-100% of the alkenyl or alkynyl functional groups react with the tetrazine monomers.

In one other embodiment, the particle may have a diameter of about 1-1000 nm. In other embodiments, the particle may have a diameter of about 1-5, 5-10, 10-20, 20-50, 50-100, 100-200, 200-500, or 500-1000 nm.

Scheme 1: Dimethyl 1,2,4,5-dihydropyridazine-3,6-dicarboxylate UV-visible absorption, fluorescence and antioxidant properties and loss of properties with oxidation.

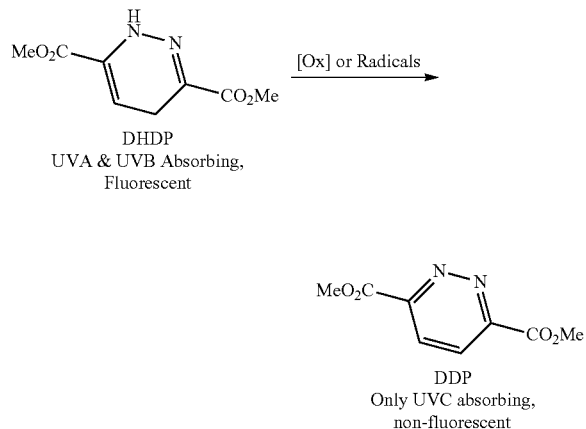

Scheme 2: Non-limiting example of formation of pyridazine monomer for organosilicon particles.

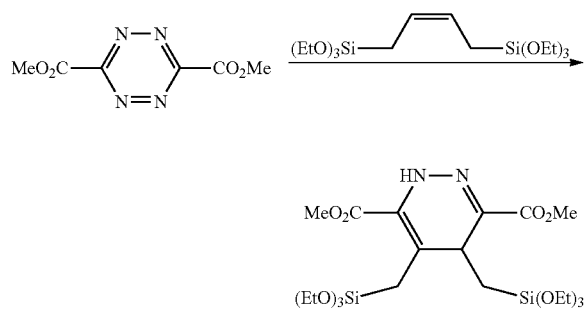

Scheme 3: Non-limiting example of sol-gel polymerization of pyridazine monomer to form organosilicon coatings or particles.

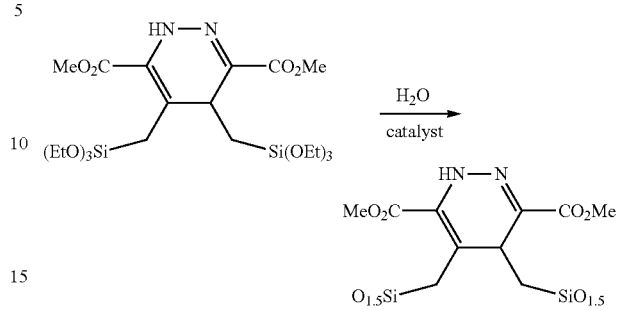

Scheme 4: Non-limiting example of formation of polymeric sunscreens by reaction of a 1,2,4,5-tetrazine monomer and a polymer with alkene functional groups.

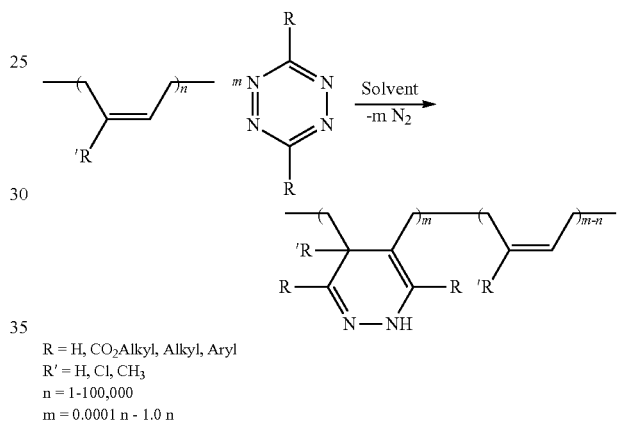

R = H, $CO_2$Alkyl, Alkyl, Aryl
R' = H, Cl, $CH_3$
n = 1-100,000
m = 0.0001 n - 1.0 n As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. An antioxidant, UVA and UVB absorbing monomer, wherein the monomer comprises a dihydropyridazine or hydropyridazine functional group, wherein the monomer further comprises at least one alkoxysilane functional group, wherein the monomer is configured to react with one or more co-monomers to form a UV absorbing organosilicon particle,
   wherein the dihydropyridazine or hydropyridazine functional groups are capable of being oxidized to one or more pyridazine functional groups by consuming one or more surrounding oxidizing species, thereby providing the monomer an ability to act as an antioxidant,
   wherein the dihydropyridazine or hydropyridazine functional groups are fluorescent and the pyridazine functional groups are less fluorescent,
   wherein an oxidation of said dihydropyridazine or hydropyridazine functional groups causes a depletion of said ability to act as an antioxidant, and wherein said oxidation can be detected by a decrease of a fluorescent intensity of said polymer.

2. The monomer of claim 1, wherein the monomer comprises at least one of the following structures:

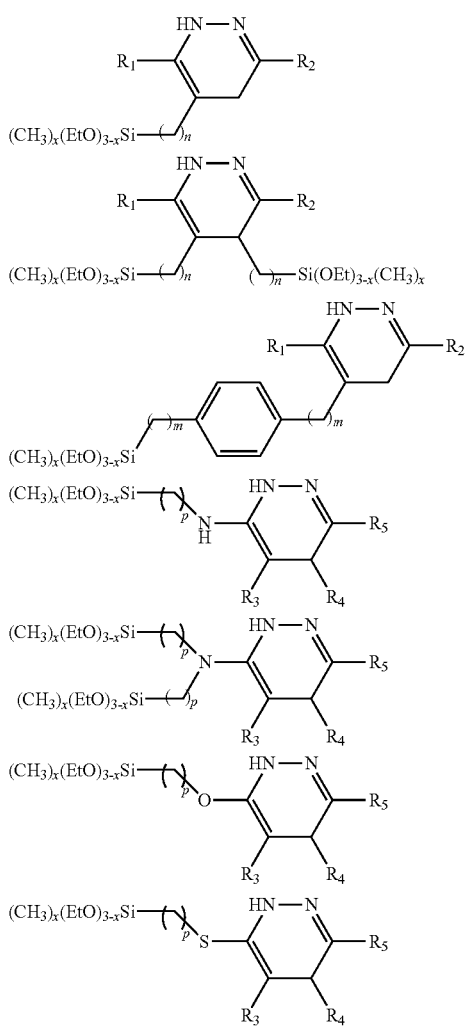

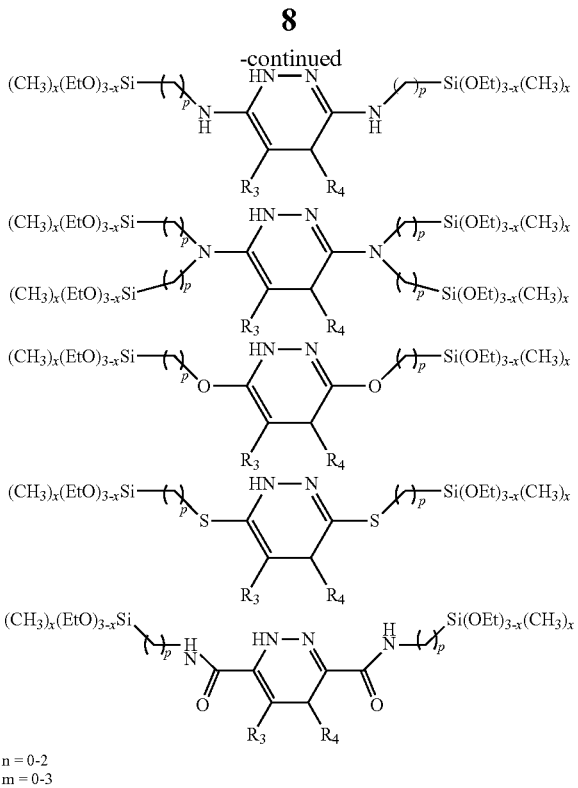

$n = 0-2$
$m = 0-3$ wherein,
$X=0-2$ $R_1=R_2$ or $R_1 \neq R_2$ $p=1-4$
$R_1$=H, alkyl, aryl, $CO_2$alkyl, NHAlkyl, Ndialkyl, Cl, Oalkyl, Oaryl, Salkyl
$R_2$=H, alkyl, aryl, $CO_2$alkyl, NHAlkyl, Ndialkyl, Cl, Oalkyl, Oaryl, Salkyl
$R_3=R_4$ or $R_3 \neq R_4$ $R_3$=H, alkyl, aryl $R_4$=H, alkyl, aryl
$R_5$=H, alkyl, aryl, Oalkyl, Salkyl, 1°, 2° alkyl or aryl amine, CN, Cl, $CO_2$alkyl.

3. The monomer of claim 1, wherein the co-monomer comprises an alkyl orthosilicate.

4. The monomer of claim 1, wherein the monomer is colorless before and after oxidation.

5. A method of forming a UV absorbing organosilicon particle, wherein the particle comprises a plurality of dihydropyridazine or hydropyridazine functional groups, and wherein the particle is configured to absorb UVA and UVB light, the method comprising:
   a. providing a UV absorbing monomer, wherein the monomer comprises a dihydropyridazine or hydropyridazine functional group, and wherein the monomer comprises at least one alkoxysilane functional group;
   b. providing an orthosilicate co-monomer; and
   c. mixing said monomer and co-monomer, wherein the monomer and co-monomer react in a condensation reaction to form said organosilicon particle.

6. The method of claim 5, wherein the UV absorbing monomer comprises a dialkyl 1,2,4,5-dihydropyridazine-3,6-dicarboxylate derivative.

7. The method of claim 5, wherein the co-monomer comprises an alkyl orthosilicate.

8. The method of claim 5, wherein a catalyst is used in a reaction between the monomer and co-monomer.

9. The method of claim 5, wherein the dihydropyridazine or hydropyridazine functional groups are capable of being oxidized to one or more pyridazine functional groups by consuming one or more surrounding oxidizing species, thereby providing the particle an ability to act as an antioxidant.

10. The method of claim 9, wherein the dihydropyridazine or hydropyridazine functional groups are fluorescent and the pyridazine functional groups are less fluorescent.

11. The method of claim 10, wherein an oxidation of said dihydropyridazine or hydropyridazine functional groups causes a depletion of said ability to act as an antioxidant, and wherein said oxidation can be detected by a decrease of a fluorescent intensity of said polymer.

12. The method of claim 11, wherein said oxidation causes the particle to have a decreased ability to absorb UV light.

* * * * *